United States Patent [19]
Hjelle et al.

[11] Patent Number: 5,919,222
[45] Date of Patent: Jul. 6, 1999

[54] ADJUSTABLE MEDICAL ELECTRODE LEAD

[75] Inventors: Mark A. Hjelle, White Beark Lake; Timothy G. Laske, Shoreview, both of Minn.

[73] Assignee: Medtronic Inc., Minneapolis, Minn.

[21] Appl. No.: 09/003,420

[22] Filed: Jan. 6, 1998

[51] Int. Cl.$^6$ ....................................................... A61N 1/05
[52] U.S. Cl. ........................... 607/122; 600/374; 600/393
[58] Field of Search ................................... 607/116, 117, 607/119, 122, 123, 124, 126–128, 132, 133, 134–138, 149; 600/372, 373–381, 393

[56] References Cited

U.S. PATENT DOCUMENTS

| | | |
|---|---|---|
| 4,106,512 | 8/1978 | Bisping . |
| 4,662,377 | 5/1987 | Heilman et al. . |
| 4,735,205 | 4/1988 | Chachques et al. . |
| 4,817,608 | 4/1989 | Shapland et al. . |
| 5,005,587 | 4/1991 | Scott . |
| 5,111,811 | 5/1992 | Smits . |
| 5,115,818 | 5/1992 | Holleman et al. . |
| 5,174,288 | 12/1992 | Bardy et al. . |
| 5,342,407 | 8/1994 | Dahl et al. . |
| 5,383,922 | 1/1995 | Zipes et al. . |
| 5,433,730 | 7/1995 | Alt . |
| 5,578,067 | 11/1996 | Ekwall et al. . |
| 5,584,873 | 12/1996 | Shoberg et al. . |
| 5,676,694 | 10/1997 | Boser et al. . |

OTHER PUBLICATIONS

U.S. Patent Application, SN 08/821,899 filed Mar. 21, 1997 by M. Hill.

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

An implantable electrical lead having an elongated lead body carrying a conductor therein and an elongated electrode extending from the lead body and coupled to the conductor. The lead is provided with an insulative tubular sheath mounted around the electrode and slideable thereon, the sheath having a length less than that of the electrode. Optionally, the sheath is provided with a mechanism for facilitating its removal from the electrode, which may take the form of a weakened zone formed in the sheath. The lead may be provided with a plurality of insulative sheaths slidably mounted around the electrode, and each sheath is preferably provided with a mechanism for stabilizing the location of the sheath along the electrode, which mechanism may function to frictionally engage the sheath with the electrode or to compress the sheath around the electrode.

9 Claims, 5 Drawing Sheets

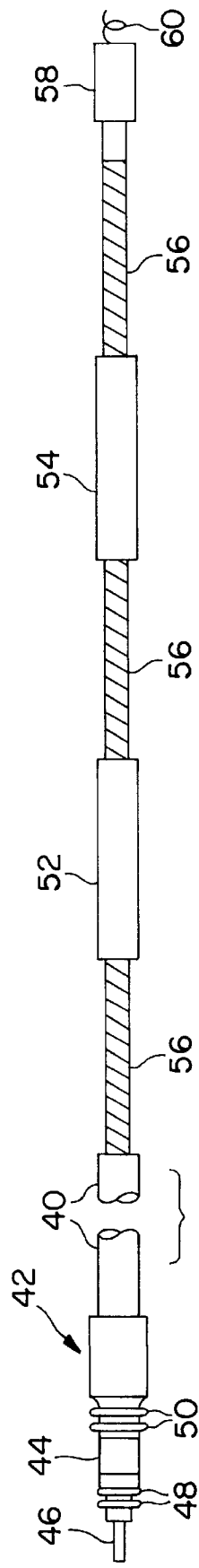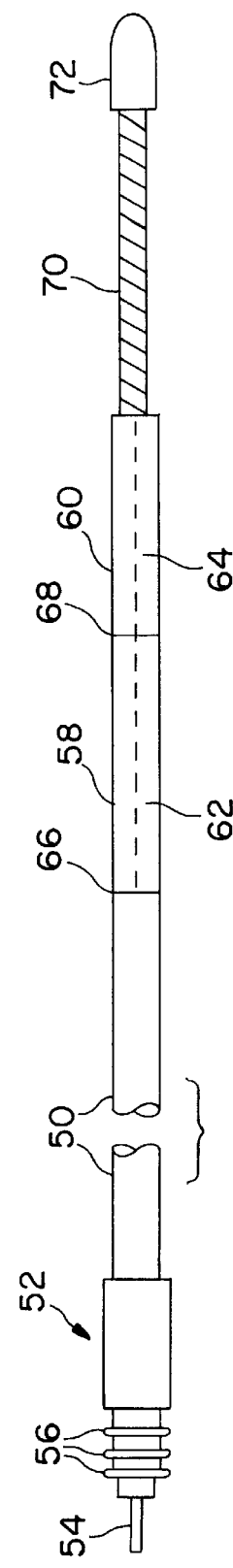
FIG. 5
FIG. 6

ADJUSTABLE MEDICAL ELECTRODE LEAD

BACKGROUND OF THE INVENTION

The present invention relates generally to implantable medical leads and more particularly to implantable cardioversion and defibrillation leads.

Implantable cardioversion/defibrillation leads are employed to deliver electric shocks to the heart to convert tachycardias and fibrillation to normal sinus rhythm. In conjunction with this function, it is desirable that the electrodes are configured and located appropriately relative to the patient's heart to accomplish cardioversion and defibrillation at the lowest possible energy levels. In order to achieve this result, quite a number of electrode configurations and locations have been proposed. For example, multiple electrode configurations are disclosed in U.S. Pat. No. 5,174,288 issued to Bardy, U.S. Pat. No. 4,817,608 issued to Shapland et al., U.S. Pat. No. 4,662,377 issued to Heilman et al. and U.S. Pat. No. 5,111,811 issued to Smits. As a practical matter, no one electrode configuration is optimal for all patients. In addition, patients' hearts may differ substantially in size and in disease states. As such, there has been interest in providing cardioversion/defibrillation leads which have some form of adjustment available to vary either the location of or the size of the cardioversion/defibrillation surface. Sliding sleeves, for example, have been employed in conjunction with the leads described in U.S. Pat. No. 4,735,205 issued to Chachques et al., U.S. Pat. No. 5,578,067 issued to Ekwall et al., U.S. Pat. No. 5,383,922 issued to Zipes et al. and pending U.S. patent application Ser. No. 08/821,899 filed on Mar. 21, 1997 by Michael Hill, for adjustment of position and/or length of cardioversion/defibrillation or other electrode surfaces.

An additional alternative approach to physically reconfiguring the location or length of the cardioversion/defibrillation electrode is to accomplish the same result electrically by selecting between different electrodes located along the length of the lead to effectively provide cardioversion/defibrillation electrodes optimized with respect to location and/or length, as disclosed in U.S. Pat. No. 5,174,288 issued to Pohndorf et al.

SUMMARY OF THE INVENTION

The present invention is directed toward providing a cardioversion/defibrillation lead with a wide degree of adjustability and flexibility with regard to the location and length of its cardioversion/defibrillation electrodes. The present invention accomplishes these results by means of a single elongated defibrillation electrode over which one or more sliding sheaths is located, each of the sheaths having a length less than that of the electrode itself. By this mechanism, movement of the sheath or sheaths relative to the electrode can be used to provide for single or multiple electrode surfaces and to vary the location and length of those surfaces along the length of the lead. In one embodiment, the sheaths are provided with a mechanism facilitating removal of the sheath, to provide additional flexibility in electrode configuration.

BRIEF DESCRIPTION OF THE DRAWINGS

FIG. 5 is a plan view of a second embodiment of the lead according to the present invention.

FIG. 6 is a plan view of a third embodiment of a lead according to the present invention.

DETAILED DESCRIPTION OF THE PREFERRED EMBODIMENTS

Figure 1:
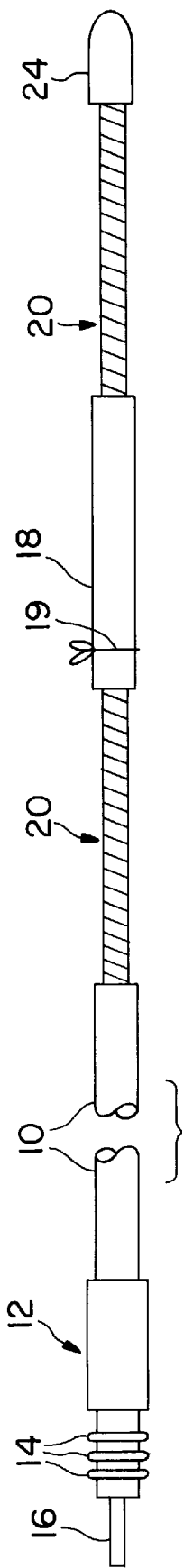
FIG. 1 is a plan view of a first embodiment of a lead according to the present invention.

FIG. 1 is a plan view of a first embodiment of a cardioversion/defibrillation lead according to the present invention. The lead is provided with an elongated insulative lead body 10 which carries an elongated conductor therein. The conductor in the lead body is coupled at its proximal end to a connector pin 16 located on a connector assembly 12 which is adapted to be inserted into the connector block of an implantable cardioversion/defibrillation. Sealing rings 14 seal connector assembly 12 within the lumen of the connector block. Coupled to the elongated conductor within lead body 10 is an elongated cardioversion/defibrillation 20, which may correspond to the coil electrodes presently employed for cardioversion/defibrillation leads, mounted to an insulative substrate as disclosed in U.S. Pat. No. 5,115,818 issued to Holleman et al. and U.S. Pat. No. 5,676,694 issued to Boser et al., incorporated herein by reference in their entireties. Alternatively, electrode 20 may take the form of an elongated stranded or braided conductor, extending from the distal end of insulative lead body 10, as disclosed in U.S. Pat. No. 5,433,730 issued to Alt or U.S. Pat. No. 5,342,407 issued to Dahl et al. or U.S. Pat. No. 5,005,587 issued to Scott., all of which are incorporated herein by reference in their entireties. The electrode 20 may be formed separately from the conductor within lead body 10 or may be an extension of the conductor within lead body 10. In the embodiment illustrated, an insulative tip 24 is provided at the distal end of the lead.

An insulative sleeve 18, which may be fabricated of silicone rubber, polyurethane or other biocompatible plastic is located around electrode 20 and may be slid proximally or distally with respect to electrode 20. As illustrated in the Figure, the sleeve 18 is located approximately in the center portion of electrode 20, effectively dividing the electrode into two separate sections. The sleeve 18, when located in this position, may be employed, for example, to provide electrodes locatable in the superior vena cava and the coronary sinus/great vein, as part of a multiple lead defibrillation system. Sliding sheath 18 proximally or distally will vary the ratio of exposed surface areas of the two electrodes, and thus vary the current distribution in the heart. Sheath 18 if slid to either the proximal end or the distal end of electrode 20 effectively will provide a single elongated electrode surface, which may be located in any of the various positions in which endocardial defibrillation electrodes are presently employed. Sleeve 18 may be constructed so that it fits snugly around electrode 20 so that its position is maintained on electrode 20 simply by friction between the two components. Alternatively, sheath 18 may be provided with internal projections or ribs which engage the defibrillation electrode 20 to stabilize its location. In addition or as an alternative, a suture 19 or other appropriate mechanism may be employed to compress sheath 18 around electrode 20.

Figure 2:
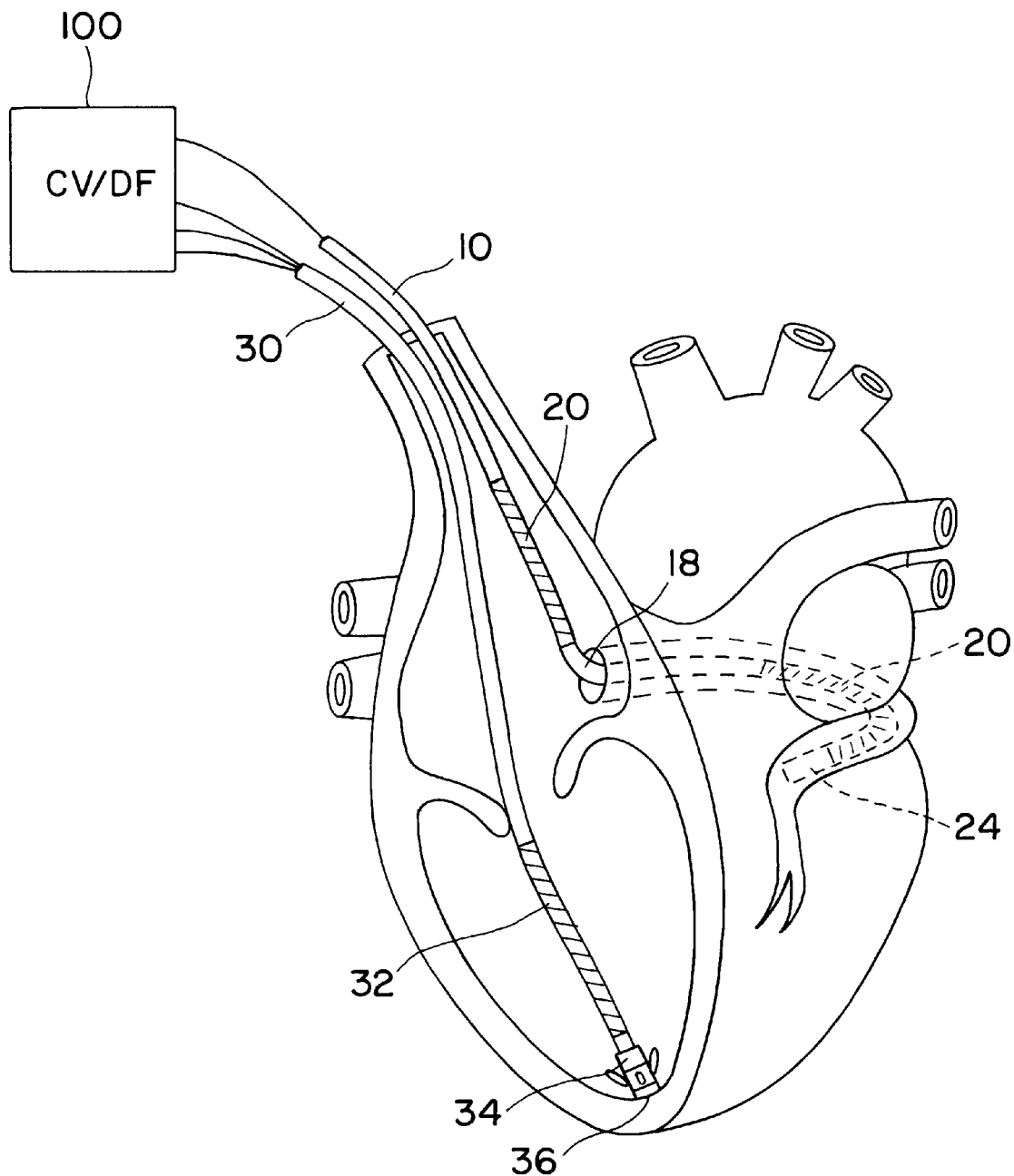
FIGS. 2, 3 and 4 illustrate the use of the lead of FIG. 1 as part of an implantable defibrillation system.

FIG. 2 illustrates the lead of FIG. 1 located in a human heart and employed in conjunction with an implantable defibrillation system including an implantable cardioverter/defibrillator 100 and an additional ventricular defibrillation lead 30. All labeled elements of the lead correspond to those in FIG. 1, as is the case for FIGS. 3 and 4, discussed below. Defibrillation lead 30 may correspond to currently available transvenous defibrillation leads, for example as disclosed in U.S. Pat. No. 5,584,873 issued to Shoberg et al. or U.S. Pat. No. 5,676,694 issued to Boser et al., both of which are incorporated herein by reference in their entireties. Lead 30 is provided with an elongated ventricular defibrillation electrode 32 and pacing/sensing electrodes 34 and 36. The lead of FIG. 1 is illustrated located in the superior vena cava and coronary sinus/great vein of the heart with insulative sheath 18 located approximately centrally along the length of elongated electrode 20. When so configured, the lead provides electrode surfaces in the superior vena cava/right atrium and the coronary sinus/great vein of the heart of the heart, spaced from one another. In this configuration, shocks would be delivered between the two exposed portions of electrode 20 and electrode 32.

Figure 3:
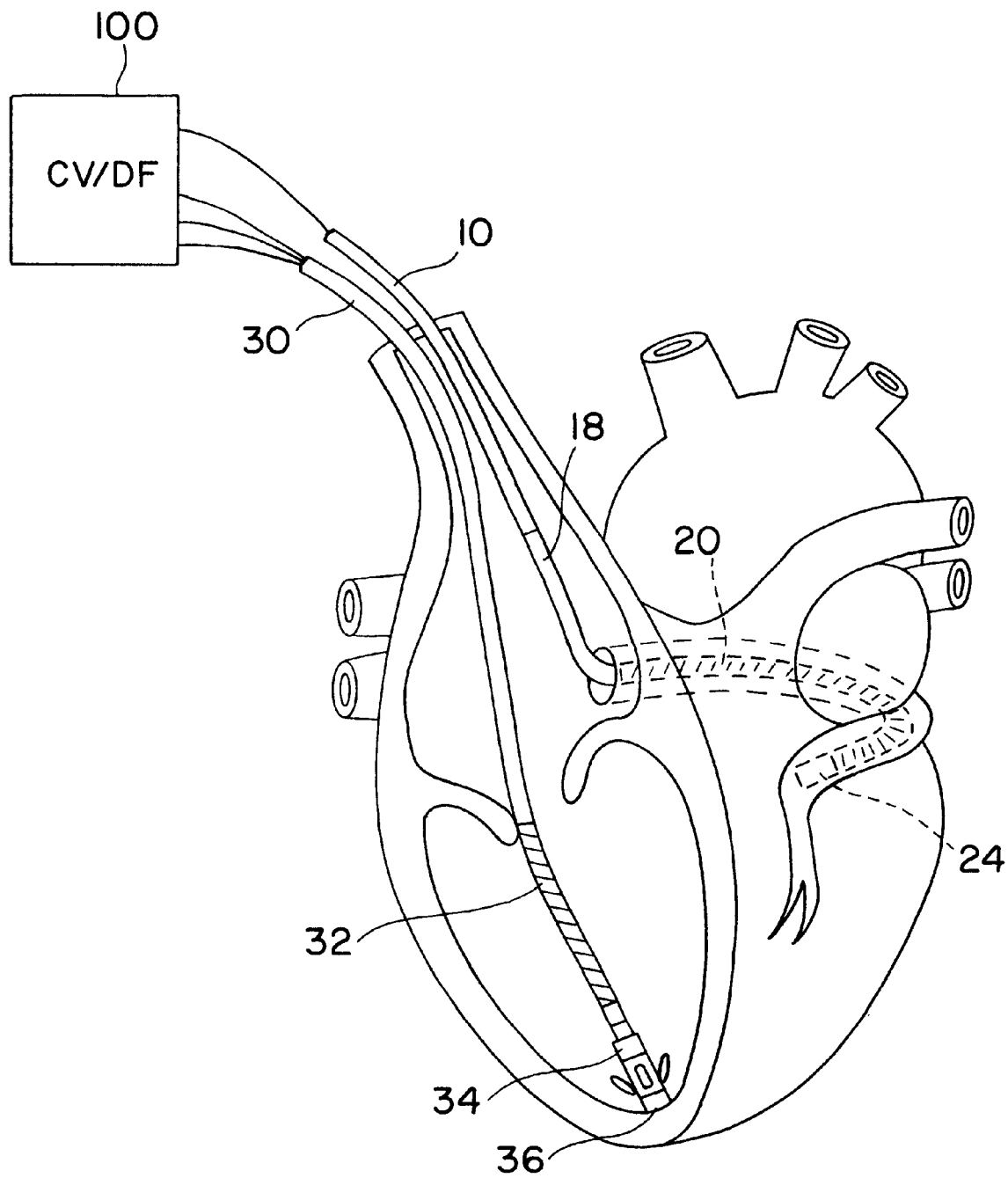

FIG. 3 illustrates an alternative use of the lead of FIG. 1 in conjunction with the cardioverter/defibrillator 100 and the lead 30 illustrated in FIG. 2. In this figure, the insulative sheath 18 is slid proximally until it abuts the distal end of lead body 10 to provide a single elongated electrode surface 20, located in the coronary sinus 20 and great vein of the heart. In this configuration, defibrillation energy is similarly delivered between electrode 20 and electrode 32, however, distribution of the electrical field differs substantially from that resulting from the lead configuration illustrated in FIG. 2.

Figure 4:
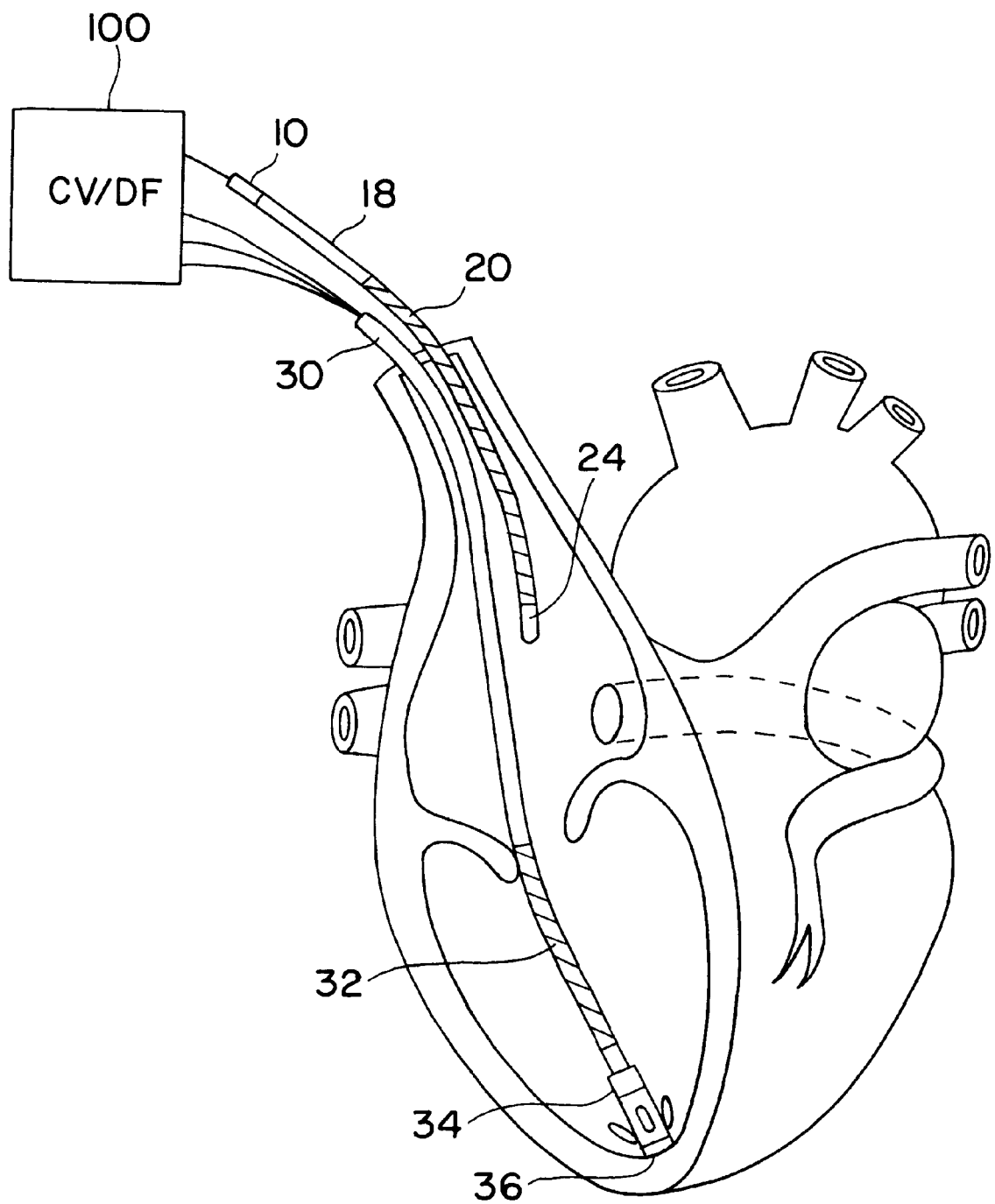

FIG. 4 is yet another alternative use of the lead of FIG. 1 in conjunction with the cardioverter/defibrillator 100 and the second lead 30 illustrated in FIG. 2. In this figure, the insulative sheath 18 is slid proximally until it abuts the distal end of insulative lead body 10, providing for a single elongated electrode surface 20, located in the superior vena cava or subclavian vein of the heart. Other arrangements and locations for the lead of FIG. 1 may also be employed.

FIG. 5 is a second embodiment of a lead according to the present invention. This lead, like the lead of FIG. 1 is provided with an elongated lead body 40 which in this case carries two elongated mutually insulated conductors therein. One of the conductors is coupled to connector pin 46 on connector assembly 42 and extends to the helical pacing/sensing electrode 60 located at the end of the lead. Electrode 60 may be rotated by means of rotation of connector pin 46, rotating the conductor coupled thereto as described in U.S. Pat. No. 4,106,512 issued to Bisping, and incorporated herein by reference in its entirety. The second conductor in lead body 40 is coupled to connector ring 44 and to an elongated electrode 56, which may be a braided or coiled electrode as described above in conjunction with electrode 20 of the lead of FIG. 1. Sealing rings 48 and 50 seal connector assembly 42 within the connector block of a cardioverter/defibrillator. The lead of FIG. 5 is provided with two sliding insulative sheaths 52 and 54 which may be adjusted to provide one, two or three electrode surfaces of varying sizes and locations along the length of the lead.

FIG. 6 is a plan view of a third embodiment of a lead according to the present invention. The lead corresponds generally to that illustrated in FIG. 1, and is provided with an elongated insulated lead body 50 carrying a connector assembly 52 which includes a connector pin 54 and sealing rings 56. Connector pin 54 is connected by means of an elongated conductor located within lead body 50 to an elongated cardioversion/defibrillation electrode 70, which may correspond to electrode 20 of the lead of FIG. 1. A plastic tip is provided at the distal end of the lead. In the lead illustrated in FIG. 6, multiple insulative sleeves 58 and 60 are provided, each of which is provided with a mechanism facilitating their removal from the lead body. In the case illustrated, a scored or weakened zone 62, 64 such as a perforation or groove may be provided, facilitating removal of the sheaths from electrode 70. The sheaths 58 and 60 may also be slid along the length of electrode 70 to provide multiple or single electrode surfaces as described in conjunction with FIG. 1 above. As illustrated, the sheaths 58 and 60 are separately formed, and simply abut one another at locations 66 and 68. However, they may instead be formed integrally with lead body 50 and provided with additional weakened zones at locations 66 and 68, facilitating their separation from each other and lead body 50.

In the embodiment illustrated in FIG. 6, the sheaths 58 and 60 may be separated from one another, slid relative to one another and to electrode 70 and removed from electrode 70 to provide a wide variety of different electrode sizes, locations and lengths.

In conjunction with the above specification, we claim:

1. An implantable electrical lead, comprising:
    an elongated lead body carrying a conductor therein;
    an elongated electrode extending from said lead body and coupled to said conductor within said lead body; and
    an insulative tubular sheath mounted around said elongated electrode and slideable thereon, said sheath having a length less than that of the electrode and provided with means for facilitating its removal from the elongated electrode, said removal facilitating means comprising a weakened zone formed in said sheath.

2. A lead according to claim 1, wherein said sheath is provided with means for facilitating its removal from the elongated electrode.

3. A lead according to claim 1 wherein said removal facilitating means comprises a weakened zone formed in said sheath.

4. An implantable electrical lead, comprising:
    an elongated lead body carrying a conductor therein;
    an elongated electrode extending from said lead body and coupled to said conductor within said lead body; and
    an insulative tubular sheath mounted around said elongated electrode and slideable thereon, said sheath having a length less than that of the electrode wherein said sheath is formed as part of said lead body and said lead is further provided with means for detaching said sheath from said lead body.

5. A lead according to claim 1 or claim 4 wherein said lead comprises a plurality of insulative sheaths slidably mounted around said electrode.

6. A lead according to claim 1 or claim 4 comprising means for stabilizing the location of said sheath along said electrode.

7. A lead according to claim 6 wherein said stabilizing means comprises means for frictionally engaging said sheath with said electrode.

8. A lead according to claim 6 wherein said stabilizing means comprises means for compressing said sheath around said electrode.

9. A lead according to claim 4 wherein said detaching means comprises a weakened zone formed in said lead body.

* * * * *